United States Patent [19]
DeGroot

[11] Patent Number: 5,366,450
[45] Date of Patent: Nov. 22, 1994

[54] AN ENVELOPED COILED TAMPON

[75] Inventor: Hans F. DeGroot, Strängnäs, Sweden

[73] Assignee: SanPoint AB, Mariefred, Sweden

[21] Appl. No.: 40,118

[22] Filed: Mar. 30, 1993

[30] Foreign Application Priority Data

Apr. 9, 1992 [EP] European Pat. Off. ............ 92106112

[51] Int. Cl.⁵ .............................................. A61F 13/15
[52] U.S. Cl. ..................................... 604/366; 604/904
[58] Field of Search ...................... 604/1.11, 358, 366, 604/370, 374, 904

[56] References Cited

U.S. PATENT DOCUMENTS 4,661,101 4/1987 Sustmann ............................ 604/904
5,006,116 4/1991 Alikhan et al. ..................... 604/370

FOREIGN PATENT DOCUMENTS 361842 4/1990 European Pat. Off. ............ 604/376
9015123.2 4/1992 Germany .

Primary Examiner—Jerome L. Kruter
Attorney, Agent, or Firm—Herbert Dubno

[57] ABSTRACT

The invention relates to a tampon for female hygiene having a wound nonwoven fabric core and an envelope with thermoplastic fibers which externally encloses the core, the envelope consisting of a nonwoven fabric which has hydrophilic fibers in addition to the thermoplastic fibers.

8 Claims, 1 Drawing Sheet

AN ENVELOPED COILED TAMPON

FIELD OF THE INVENTION

The present invention relates to a tampon for female hygiene, having a wound nonwoven fabric core and an envelope with thermoplastic fibers which externally encloses the core.

BACKGROUND OF THE INVENTION

Tampon envelopes are known which are all-synthetic and have hydrophobic properties. To avoid leakage, the envelope must always be connected over a large area to the absorbing core, so that an expensive support is required.

OBJECT OF THE INVENTION

It is an object of the invention to provide a tampon of the kind specified which is simple to produce and offers the certainty that when the envelope is used—i.e., becomes wet—it immediately applies itself closely to the absorbing core, thereby preventing any leakage between the envelope and the core.

SUMMARY OF THE INVENTION

This problem is solved according to the invention in a tampon in which the envelope consists of a nonwoven fabric which has hydrophilic fibers in addition to the thermoplastic fibers.

Such a tampon is inexpensive to produce and offers high security when used. When it becomes wet, due to the softening of the hydrophilic cellulose fibers component the envelope applies itself closely to the core, thus achieving optimum behavior. As a result of the hydrophilic nature of the envelope, not only is liquid very quickly absorbed and quickly passed on via the closely-fitting support to the core, but there is no need for the envelope to be welded to the core completely over a large area. On the contrary, it is enough for the envelope to be connected to the core via a single connecting place which can be linear or strip-shaped and is preferably disposed transversely of the longitudinal direction of the wound core band.

Very importantly the connecting place is externally covered by a wound layer. Also according to the invention the width of the envelope is equal to the length of the tampon. This substantially reduces the risk of the fibers becoming loosened during use.

Particularly advantageously the hydrophilic fibers make up a proportion of 10 to 80 per cent, more particularly approximately 50 per cent of the envelope. The hydrophilic fibers can advantageously consist of cellulose, more particularly viscose fiber or cotton.

BRIEF DESCRIPTION OF THE DRAWING

An embodiment of the invention will now be described in greater detail with reference to the drawing, wherein.

Figure 1:
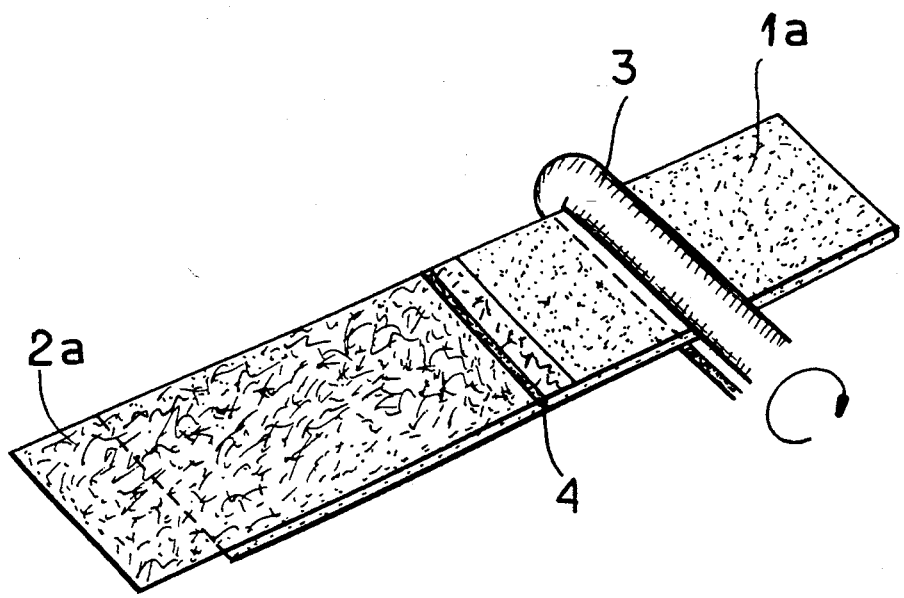
FIG. 1 is a perspective view of the core band with the envelope band secured thereon and a winding fork pushed thereover.
Figure 2:
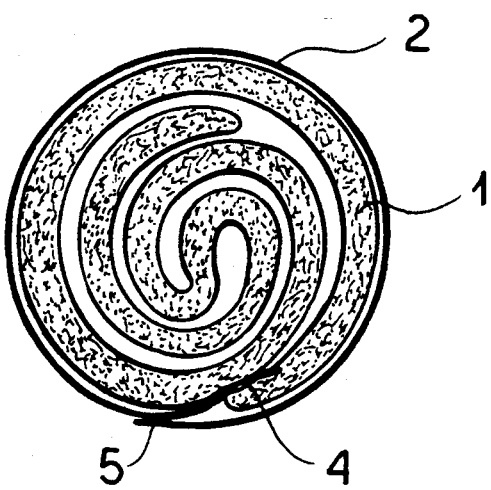
FIG. 2 is a cross-section through the tampon in the wound state prior to compression.

A tampon has an inner, substantially cylindrical core 1 and an envelope 2 externally enclosing said core. The core 1 is wound from a cotton-wool band 1a using a winding fork 3 and consists of absorptive natural and/or artificial fibers.

The envelope 2 consists of an envelope band 2a which is wound around the core 1 and consists of a nonwoven fabric. The nonwoven fabric consists of a mixture of thermoplastic and hydrophilic fibers, the proportion of hydrophilic fibers, which can be viscose fiber or cotton amounting to 10–80 per cent, more particularly approximately 50 per cent.

All types of thermoplastic fibers are suitable which can be welded under heat and pressure. These include more particularly polyethylene or polypropylene fibers (homogeneous or heterophilic) or other fibers having a high-melting core and a low-melting envelope, for example, a polyester core and a polyethylene sheath (so-called heterophilic or bicomponent fiber).

The hydrophilic fibers of the envelope 2 consist of cellulose, more particularly viscose fiber or cotton.

The envelope band 2a is secured to the core band 1a via a welding place 4 which is disposed as a welding seam transversely of the longitudinal direction of the bands 1a, 2a, the envelope band 2a covering the core band 1a over its width and projecting beyond the cotton-wool band at the outer end only far enough to enable the envelope band 2a to be attached to itself in the wound state, more particularly via welding spots or a welding line.

The welding place 4 is therefore situated far enough inside the core winding for the welding place to be covered by the outer end of the core band 1a.

I claim:

1. A female hygiene tampon having an absorptive body consisting of:
   a core of a coiled nonwoven fabric strip;
   a water-permeable envelope formed from a nonwoven band consisting of 10 to 80% hydrophilic fibers and the balance thermoplastic fibers wound around said core, said envelope closely fitting around said core upon wetting of the envelope; and
   a single weld line securing said envelope to said core at one end of said band, said band overlapping a turn of the envelope at a free end of the band opposite said one end of said band.

2. The female hygiene tampon defined in claim 1 wherein said band consists of about 50% hydrophilic fibers, the balance being said thermoplastic fibers.

3. The female hygiene tampon defined in claim 1 wherein the hydrophilic fibers are constituted of cellulose.

4. The female hygiene tampon defined in claim 3 wherein said hydrophilic fibers are viscose fibers.

5. The female hygiene tampon defined in claim 3 wherein said hydrophilic fibers are cotton fibers.

6. The female hygiene tampon defined in claim 3 wherein said weld line extends transversely of the longitudinal dimensions of said strip and said band.

7. The female hygiene tampon defined in claim 6 wherein said free end covers said weld line.

8. The female hygiene tampon defined in claim 1 wherein said envelope has a width equal to a length of said body.

* * * * *